United States Patent [19]

Chin

[11] 4,452,244
[45] Jun. 5, 1984

[54] ENDARTERECTOMY ROLLER

[75] Inventor: Albert K. Chin, San Francisco, Calif.

[73] Assignee: Thomas J. Fogarty, Palo Alto, Calif.

[21] Appl. No.: 114,981

[22] Filed: Jan. 24, 1980

[51] Int. Cl.³ .............................................. A61B 17/00
[52] U.S. Cl. ................................. 128/321; 128/303 R;
128/346
[58] Field of Search ............... 128/321, 322, 325, 346,
128/303 R, 305, 319, 57, 60; 81/421-423;
24/244; 251/6; 193/37; 403/DIG. 4, 165, 164;
29/110.5, 116 R, 123, 129.5

[56] References Cited

U.S. PATENT DOCUMENTS

| 434,262 | 8/1890 | Freeman | 29/129.5 X |
| 1,519,693 | 12/1924 | Moore | 128/57 |

FOREIGN PATENT DOCUMENTS 278763 10/1951 Switzerland ........................ 128/321

Primary Examiner—Michael H. Thaler
Attorney, Agent, or Firm—Limbach, Limbach & Sutton

[57] ABSTRACT

An endarterectomy roller adapted to strip cores of atheromatous plaque from arteries is provided with disposable roller elements and with novel quick connect and disconnect elements for the roller elements.

2 Claims, 6 Drawing Figures

ENDARTERECTOMY ROLLER

BACKGROUND OF THE INVENTION

The invention relates to an endarterectomy instrument, namely, an endarterectomy roller, which is used to strip an extended core of atheromatous plaque from the surrounding artery prior to the removal of the core through a distal arteriotomy incision. This endarterectomy method is shown and described in the co-pending application of Thomas J. Fogarty, Ser. No. 114,980, filed Jan. 24, 1980, now U.S. Pat. No. 4,287,890 for "Endarterectomy Method and Apparatus".

The material prior art known to us consists of U.S. Pat. Nos. 3,648,701 and 4,164,223 which disclose rotatable tube-stripping rollers on forcep and surgical instruments.

SUMMARY OF THE INVENTION

The object of the invention is to provide an endarterectomy roller in which the roller elements are disposable and readily replaceable.

Another object of the invention is to provide an endarterectomy roller in which disposable roller elements may be simply snapped into place and out of place.

DESCRIPTION OF THE PREFERRED EMBODIMENT

Figure 1:
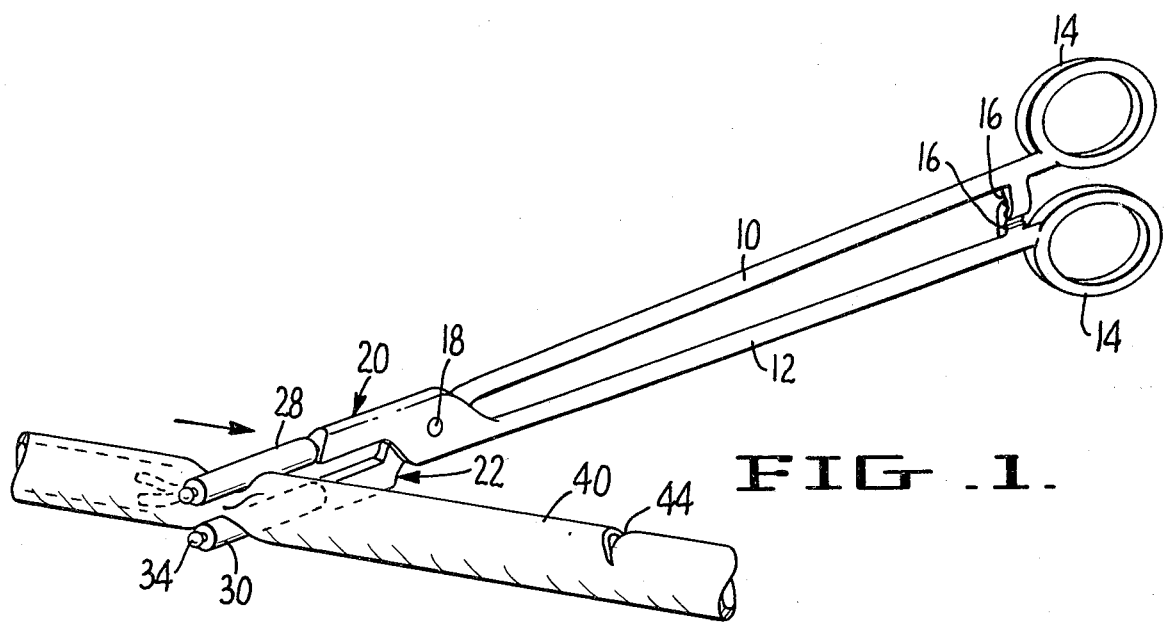
FIG. 1 is a view in perspective of the present endarterectomy roller in use during an endarterectomy.

The endarterectomy roller comprises a scissors-type instrument having arms 10 and 12, finger loops 14 and stop members 16 carried thereby, pivotal connection 18, and working arms 20 and 22 which are integral, respectively, with arms 12 and 10 and which are provided with integral pintle extensions 24 and 26. Rotatably disposed on pintles 24, 26 are roller sleeves 28 and 30. The sleeves are removably retained on the pintles by means comprising partially closed tips 32 on the sleeves, rounded ends 34 for the pintles, and annular grooves 36 formed in the pintles adjacent the pintle ends or tips 34.

The sleeves 28 and 30 are preferably made from heat shrinkable plastic tubing material, the roller pieces being heat treated at one end to form the plurality closed tips 32. The tips 32 are sufficiently flexible so that the sleeves may be readily installed and removed by snapping the ends 32 over the pintle ends 34 into the grooves 36 and out of the grooves over the pintle ends.

The scissor-type tool is made of stainless steel and the sleeves 28 and 30 are made of disposable plastic material. A complete sterile instrument is therefore afforded for each operational use by sterilization of the scissor tool in the usual manner and the packaging of the new, replacement sleeves under sterile conditions in a disposable envelope.

Figure 2:
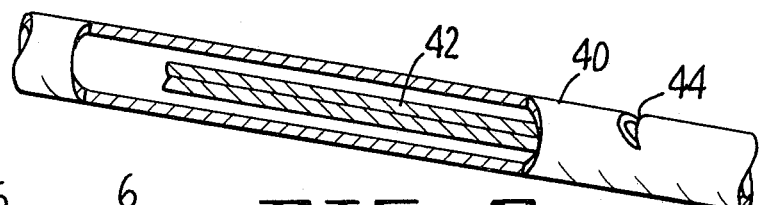
FIG. 2 is a view of the artery of FIG. 1 after stripping of the plaque has been effected by the roller.
Figure 3:
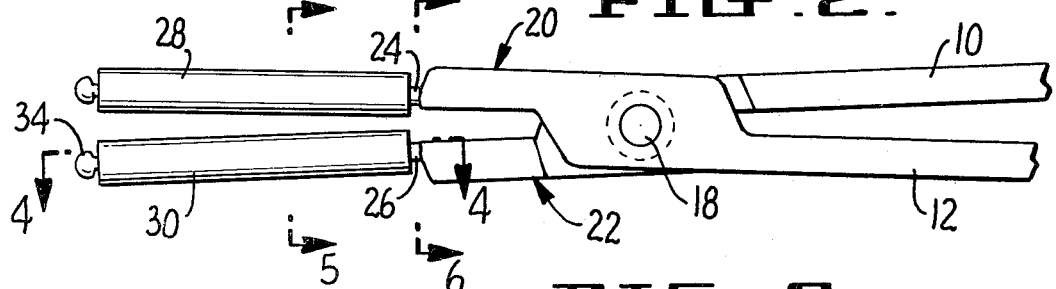
FIG. 3 is an enlarged view in side elevation of the working end of the subject instrument.
Figure 4:
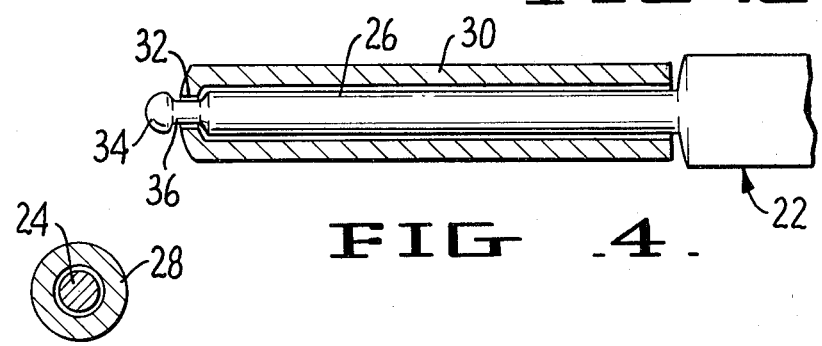
FIG. 4 is an enlarged view taken along lines 4—4 of FIG. 3.
Figure 5:
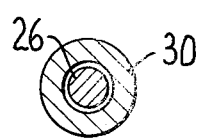
FIG. 5 is a view taken along lines 5—5 of FIG. 3.
Figure 6:
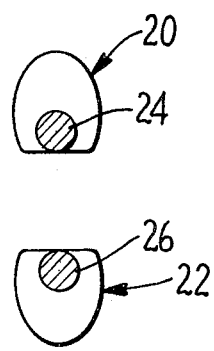
FIG. 6 is a view taken along lines 6—6 of FIG. 3.

The manner of use of the instrument is shown in FIGS. 1 and 2 and is more fully described in the previously mentioned co-pending patent application. The method of use comprises clamping artery 40 and moving the clamped instrument along the artery to strip the core of plaque 42 from the artery and enable its removal through incision 44.

What is claimed is:

1. An endarterectomy roller comprising a pair of jaw members interconnected for relative pivotal movement toward and away from each other and comprising pintle members carried thereby, elongated flexible and disposable plastic sleeve members freely fitted over said pintle members and adapted to be substantially freely rotatable thereon, and means interconnecting said sleeve members and pintle members enabling a quick connection and disconnection therebetween by the expedient of, respectively, simply axially pulling said sleeve members off of said pintle members and simply axially pushing said sleeve members onto said pintle members, said means comprising flexible annular tongue means extending from one pair of the pairs of sleeve and pintle members and complemental annular grooves formed in the other pair thereof and adapted to be snap-fittingly engaged and disengaged with respect to said tongue means.

2. The endarterectomy roller of claim 1, said tongue means comprising inwardly directed flanges formed on the outer ends of said sleeve members, said grooves being formed in said pintle members adjacent the outer ends thereof, the outer ends of said pintle members being rounded and the outer sides of said grooves being bevelled to facilitate snap-fitting connection and disconnection between said flanges and said grooves.

* * * * *